(12) United States Patent
Kemp et al.

(10) Patent No.: US 7,324,661 B2
(45) Date of Patent: Jan. 29, 2008

(54) COMPUTER-IMPLEMENTED SYSTEM AND METHOD FOR AUTOMATED AND HIGHLY ACCURATE PLAQUE ANALYSIS, REPORTING, AND VISUALIZATION

(75) Inventors: James Herbert Kemp, Somerset, NJ (US); Ashit Talukder, Simi Valley, CA (US); James Lambert, Sunland, CA (US); Raymond Lam, Arcadia, CA (US)

(73) Assignee: Colgate-Palmolive Company, New Yrok, NY (US)

( * ) Notice: Subject to any disclaimer, the term of this patent is extended or adjusted under 35 U.S.C. 154(b) by 771 days.

(21) Appl. No.: 10/836,567

(22) Filed: Apr. 30, 2004

(65) Prior Publication Data

US 2005/0244794 A1    Nov. 3, 2005

(51) Int. Cl.
 *G06K 9/00* (2006.01)
(52) U.S. Cl. ............... 382/100; 128/922; 424/9.71
(58) Field of Classification Search .............. 382/100, 382/128, 181, 190; 128/922; 424/9.71
See application file for complete search history.

(56) References Cited

U.S. PATENT DOCUMENTS

| | | | |
|---|---|---|---|
| 6,188,776 B1* | 2/2001 | Covell et al. ............... 382/100 |
| 7,068,825 B2* | 6/2006 | Rubbert et al. ............. 382/128 |
| 7,168,954 B2* | 1/2007 | Charles et al. .............. 434/263 |
| 2003/0156788 A1* | 8/2003 | Henning ....................... 385/31 |
| 2004/0151369 A1* | 8/2004 | Schwotzer ................... 382/154 |
| 2004/0236232 A1* | 11/2004 | Jonusauskas et al. ....... 600/477 |
| 2004/0259058 A1* | 12/2004 | Tosaki et al. ............... 433/215 |
| 2006/0228010 A1* | 10/2006 | Rubbert et al. ............. 382/128 |
| 2006/0270935 A1* | 11/2006 | Ariff et al. .................. 600/437 |

* cited by examiner

*Primary Examiner*—Samir Ahmed
*Assistant Examiner*—Anand Bhatnagar
(74) *Attorney, Agent, or Firm*—Michael Wallace, Jr.

(57) ABSTRACT

A computer-implemented system and method of intra-oral analysis for measuring plaque removal is disclosed. The system includes hardware for real-time image acquisition and software to store the acquired images on a patient-by-patient basis. The system implements algorithms to segment teeth of interest from surrounding gum, and uses a real-time image-based morphing procedure to automatically overlay a grid onto each segmented tooth. Pattern recognition methods are used to classify plaque from surrounding gum and enamel, while ignoring glare effects due to the reflection of camera light and ambient light from enamel regions. The system integrates these components into a single software suite with an easy-to-use graphical user interface (GUI) that allows users to do an end-to-end run of a patient record, including tooth segmentation of all teeth, grid morphing of each segmented tooth, and plaque classification of each tooth image.

28 Claims, 9 Drawing Sheets

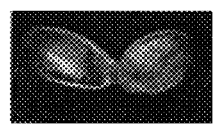 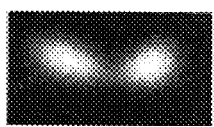 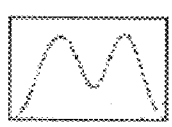 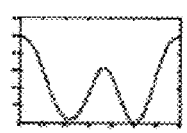
FIG. 4A   FIG. 4B   FIG. 4C   FIG. 4D
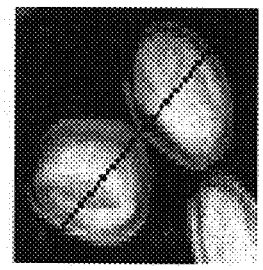 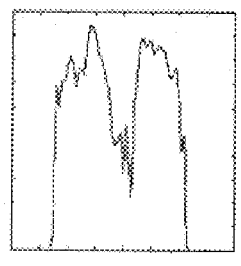 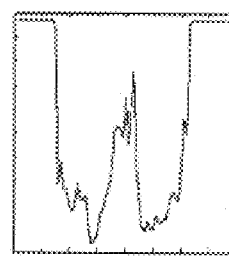
FIG. 5A   FIG. 5B   FIG. 5C
FIG. 5D

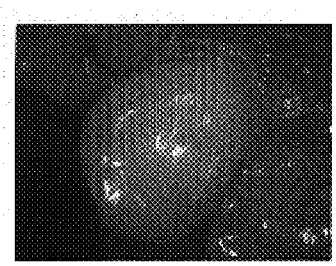
Fig. 6A
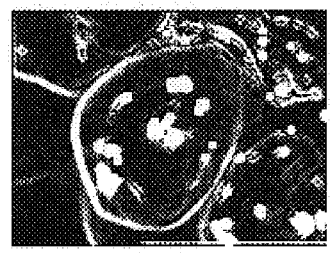
Fig. 6B
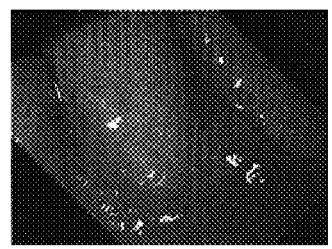
Fig. 6C
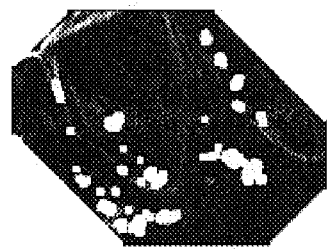
Fig. 6D
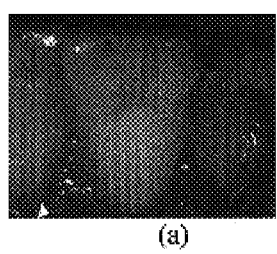
(a)
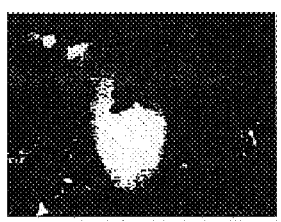
(b)
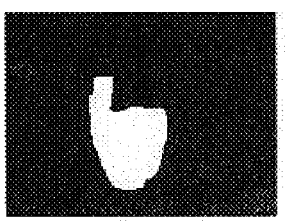
(c)
Figs. 7A-7C

 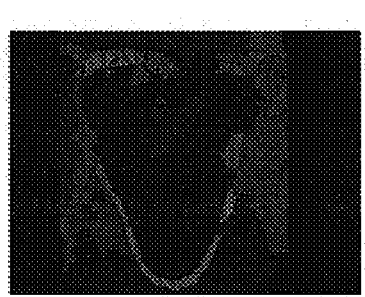
Fig. 8A Fig. 8B
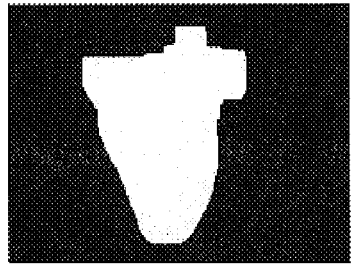
Fig. 8C
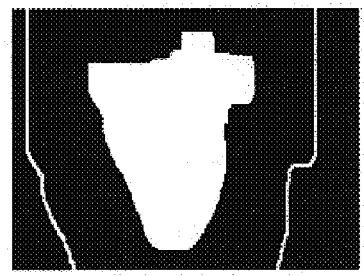 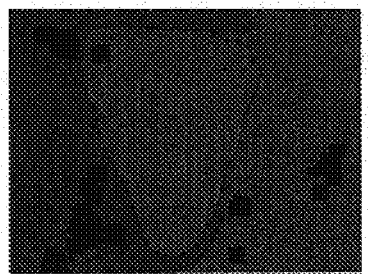
Fig. 9A Fig. 9B
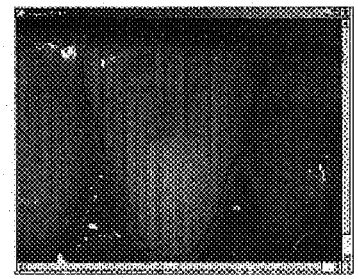
Fig. 9C

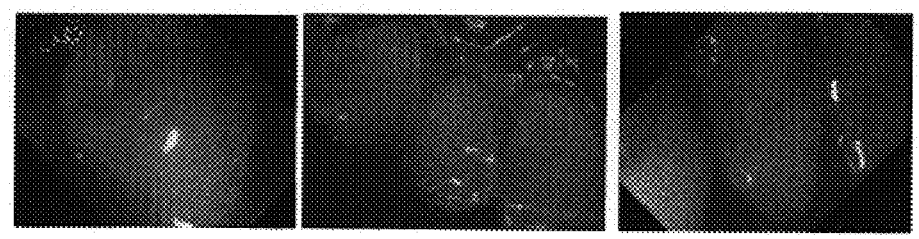
Fig. 12A
Fig. 12B
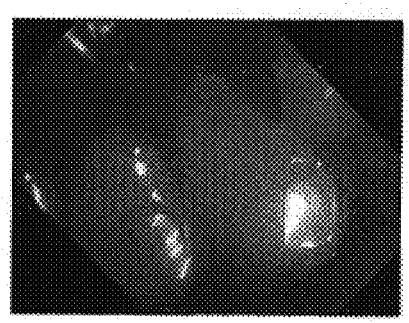 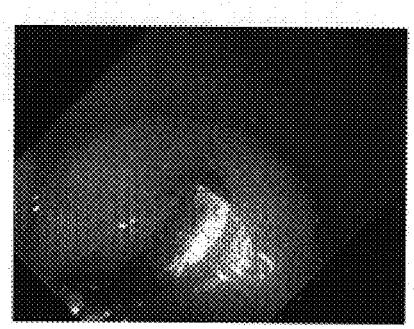
Fig. 13A                    Fig. 13B

COMPUTER-IMPLEMENTED SYSTEM AND METHOD FOR AUTOMATED AND HIGHLY ACCURATE PLAQUE ANALYSIS, REPORTING, AND VISUALIZATION

The invention described herein was made in the performance of work under a NASA contract, and is subject to the provisions of Public Law 96-517 (35 U.S.C. § 202) in which the Contractor has elected to retain title.

BACKGROUND OF THE INVENTION

A. Field of the Invention

The present invention relates generally to plaque removal and whitening capabilities for toothbrushes and toothpastes, and, more particularly to a computer-implemented system and method for automatically evaluating the efficacy of plaque removal and whitening capabilities for different toothbrushes and toothpastes.

B. Description of the Related Art

Gum (or periodontal) disease, including dental plaque, is problematic in American and European households. Almost seventy-five percent of Americans and Europeans suffer from gum disease and plaque to some extent. While removal of plaque using dental cleaning devices is an effective method for plaque control, such removal techniques require frequent visits to the dentists which are time-consuming and expensive. Brushing one's teeth is one of the most economical and time-effective method of plaque control. However, negligible work has been done on the analysis of the efficaciousness of tooth brushing methods to maintain gingival health. While the toothbrush features that control plaque removal, such as, e.g., handle size, head size, bristle configurations, bristle patterns, etc. are well-known, no work has been done to date on the efficacy of brush design for plaque removal on a tooth-by-tooth basis.

Recently, a system to determine plaque removal efficacy was implemented. The system measured the plaque on teeth as disclosed by the fluorescence of the teeth under ultraviolet ("UV") light. UV light makes plaque on teeth fluoresce as a yellow color, enamel as a light blue color, gum as a black color, and plaque on gum as a green color. In the system a set of each patient's front teeth was visually and manually overlaid with a synthetic template set for alignment, and then a digital image of the manually-aligned teeth was obtained. A simple Mahalanobis-distance based classifier was used to classify each pixel as plaque or enamel. The Mahalanobis distance is a very useful algorithm for determining the similarity of a set of values from an unknown sample to a set of values measured from a collection of known samples. The ratio of plaque versus enamel yielded a measure of percentage plaque on each patient for all the teeth combined. Resultant analyses before and after brushing allowed a measure of the efficacy of plaque removal for each toothbrush.

This system suffers from several drawbacks. First, it does not measure plaque removal efficacy for each tooth, and does not consider plaque measurements from teeth inside the mouth or on the inner (i.e., lingual) tooth surface. This is a significant disadvantage since some toothbrushes could remove plaque from teeth at the front of the mouth, but not remove plaque from the teeth in the interior of the mouth due to insufficient reach. Second, the alignment procedure of the system is visually performed and inconsistent since individual teeth vary widely from the synthetic set used in the system.

Recently, a robot-based brushing system was introduced to test plaque removal on synthetic teeth ("typodonts"). Synthetic plaque was coated onto the typodonts and different brush heads were used to brush the synthetic teeth using the robot-based brushing system. A simple image processing system was used to measure the plaque remaining after brushing. The image processing task was simple because the plaque on teeth could be easily distinguished from enamel and gum using the RGB values. Though this system is consistent since the brushing action does not vary much, the use of synthetic plaque is not realistic and does not reflect the presence of plaque on real teeth accurately. Nor does the system accurately reflect brushing actions in the mouth where the hard-to-reach teeth typically get brushed less than the front teeth.

Thus there is a need in the art for an automated system for analyzing plaque and whitening on a tooth-by-tooth basis in real-time to assist in the determination of the usefulness of new toothbrushes and toothpastes.

SUMMARY OF THE INVENTION

The present invention satisfies this need by providing a computer-implemented system and method for automatically evaluating the efficacy of plaque removal and whitening capabilities for different toothbrushes and toothpastes. The system and associated algorithms allow plaque analysis on a tooth-by-tooth basis in real-time, thereby facilitating clinical evaluation of the effectiveness of different model toothbrush designs for plaque-removal efficacy for each individual tooth and sub-regions within each tooth, prior to mass-manufacture of the toothbrush.

Additional advantages of the invention will be set forth in part in the description which follows, and in part will be learned from the description, or may be learned by practice of the invention. The advantages of the invention will be realized and attained by means of the elements and combinations, and equivalents thereof, particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one (several) embodiment(s) of the invention and together with the description, serve to explain the principles of the invention. In the drawings:

FIG. 4A is an image showing two touching agricultural products;

FIG. 4B is an image showing a distance transform image of FIG. 4A;

FIG. 4C is a graph showing the basins produced by the cross section of the agricultural products shown in FIG. 4A;

FIG. 4D is a graph showing the complement of the cross-sectional graph shown in FIG. 4C;

FIG. 5A is an image showing two touching objects having a large gray-scale variation;

FIG. 5B is a graph showing the basins produced by the cross section of the objects shown in FIG. 5A;

FIG. 5C is a graph showing the complement of the cross-sectional graph shown in FIG. 5B;

FIG. 5D is an image of teeth having low contrast boundaries;

FIG. 6A is an image of a high-contrast tooth where the enamel-gum boundary is clearly visible;

FIG. 6B is a Gabor edge-normalized output image of the image shown in FIG. 6A;

FIG. 6C is a tooth image with low-contrast between the enamel-gum boundary;

FIG. 6D is a Gabor edge-normalized output image of the image shown in FIG. 6C;

FIG. 7A is an image of a tooth under examination by the system and method of the present invention;

FIG. 7B is an image of the brightest regions of the tooth image shown in FIG. 7A;

FIG. 7C is an image showing the central bright or seed region of the tooth image shown in FIG. 7A;

FIG. 8A is an image showing how the central seed region of FIG. 7C is used on an edge map of the image shown in FIG. 7A;

FIG. 8B is an image showing how the central seed region is grown to yield the segmented image;

FIG. 8C is an image showing how the central seed region is grown to yield the central segmented region;

FIG. 9A is an image showing the seed background region of image shown in FIG. 8C;

FIG. 9B is an image showing how the seed background and foreground regions are grown to yield the final segmented region;

FIG. 9C is an image showing how the final segmented region of FIG. 9B is superimposed upon the color image of the tooth;

FIGS. 12A and 12B are images showing a comparison between the dual watershed segmentation algorithm of the present invention (FIG. 12A) and the conventional watershed segmentation algorithm (FIG. 12B);

FIGS. 13A and 13B are images showing examples of undersegmentation and oversegmentation, respectively;

DESCRIPTION OF THE EMBODIMENTS OF THE INVENTION

Reference will now be made in detail to the present embodiments of the invention, examples of which are illustrated in the accompanying drawings. Wherever possible, the same reference numbers will be used throughout the drawings to refer to the same or like parts.

The present invention is broadly drawn to a computer-implemented system and method for automatically evaluating the efficacy of plaque removal and whitening capabilities for different toothbrushes and toothpastes. The system and method allow automated plaque analysis for every tooth in a patient for both, lingual and buccal surfaces. The system and method provide swift capturing and storing of each tooth image, and automatic indexing of each tooth image for retrieval in the future. The system utilizes segmentation algorithms for segmenting (i.e., separating) each tooth from surrounding teeth, and classification utilities for classifying plaque regions.

The system and method allow automated division of a tooth into several regions called grids. Plaque measurements can be made on each grid. Advanced computer graphics morphing procedures are used to graphically morph a grid onto a real tooth based on an ideal grid drawn on a synthetic tooth. The entire set of processing operations (including segmentation, grid-morphing, classification, and plaque analyses for different teeth and grid combinations) for teeth in a patient (sixty-four teeth including buccal and lingual surfaces) is typically accomplished in three to six minutes, well within the goals of clinical trials for brush evaluation. Another distinct advantage of the system and method of the present invention is that the images and associated results can be retrieved at any time, thereby allowing comparisons of different studies and brushes taken at different times.

Figure 1:
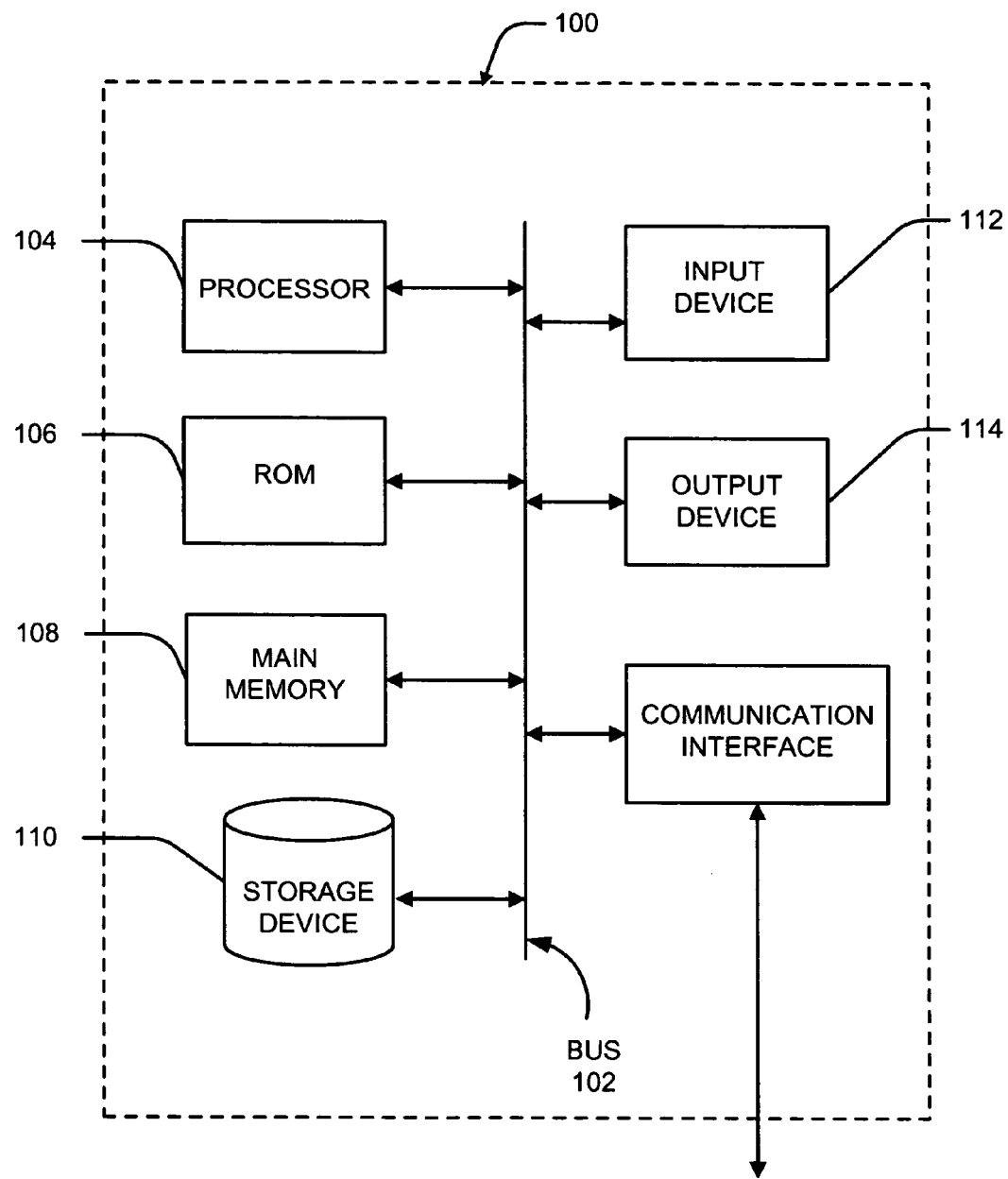
FIG. 1 is a schematic diagram showing a computing entity useful in the system and method of the present invention.

In accordance with the invention and as shown in FIG. 1, the system of the present invention includes a conventional computing entity 100, or a series of connected conventional computing entities. Each computing entity 100 may include a bus 102 interconnecting a processor 104 a read-only memory (ROM) 106, a main memory 108, a storage device 110, an input device 112, an output device 114, and a communication interface 116. Bus 102 is a network topology or circuit arrangement in which all devices are attached to a line directly and all signals pass through each of the devices. Each device has a unique identity and can recognize those signals intended for it. Processor 104 includes the logic circuitry that responds to and processes the basic instructions that drive the computer. ROM 106 includes a static memory that stores instructions and date used by processor 104.

Computer storage is the holding of data in an electromagnetic form for access by a computer processor. Main memory 108, which may be a RAM or another type of dynamic memory, makes up the primary storage of the computer. Secondary storage of the computer may comprise storage device 110, such as hard disks, tapes, diskettes, Zip drives, RAID systems, holographic storage, optical storage, CD-ROMs, magnetic tapes, and other external devices and their corresponding drives.

Input device 112 may include a keyboard, mouse, pointing device, sound device (e.g. a microphone, etc.), biometric device, or any other device providing input to the computer. Output device 414 may comprise a display, a printer, a sound device (e.g. a speaker, etc.), or other device providing output to the computer. Communication interface 116 may include network connections, modems, or other devices used for communications 118 with other computer systems or devices.

As will be described below, computing entity 100 consistent with the present invention may make be part of the system of the present invention and perform the method of the present invention to automatically evaluate the efficacy of plaque removal and whitening capabilities for different toothbrushes and toothpastes in accordance with the present invention. Computing entity 100 performs this task in response to processor 104 executing sequences of instructions contained in a computer-readable medium, such as main memory 108. A computer-readable medium may include one or more memory devices and/or carrier waves.

Execution of the sequences of instructions contained in main memory 108 causes processor 104 to perform processes that will be described later. Alternatively, hardwired circuitry may be used in place of or in combination with software instructions to implement processes consistent with the present invention. Thus, the present invention is not limited to any specific combination of hardware circuitry and software.

The system and method of the present invention permit swift capture of clinical image data for plaque and gingival analysis, automated processing and generation of plaque classification results for each patient and across different patients in a study. The entire set of operations is wrapped in an easy-to-use graphical user interface (GUI) that keeps the details of the implementation hidden from users, and allows people not conversant with computers to easily use the system with a minimal learning curve.

Figure 2A:
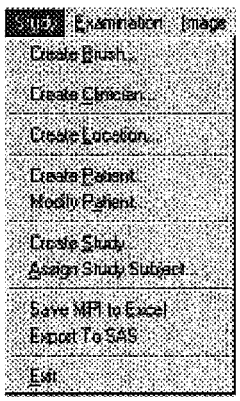
FIGS. 2A-2C are screenshots showing some of the software features of the system and method of the present invention.
Figure 2B:
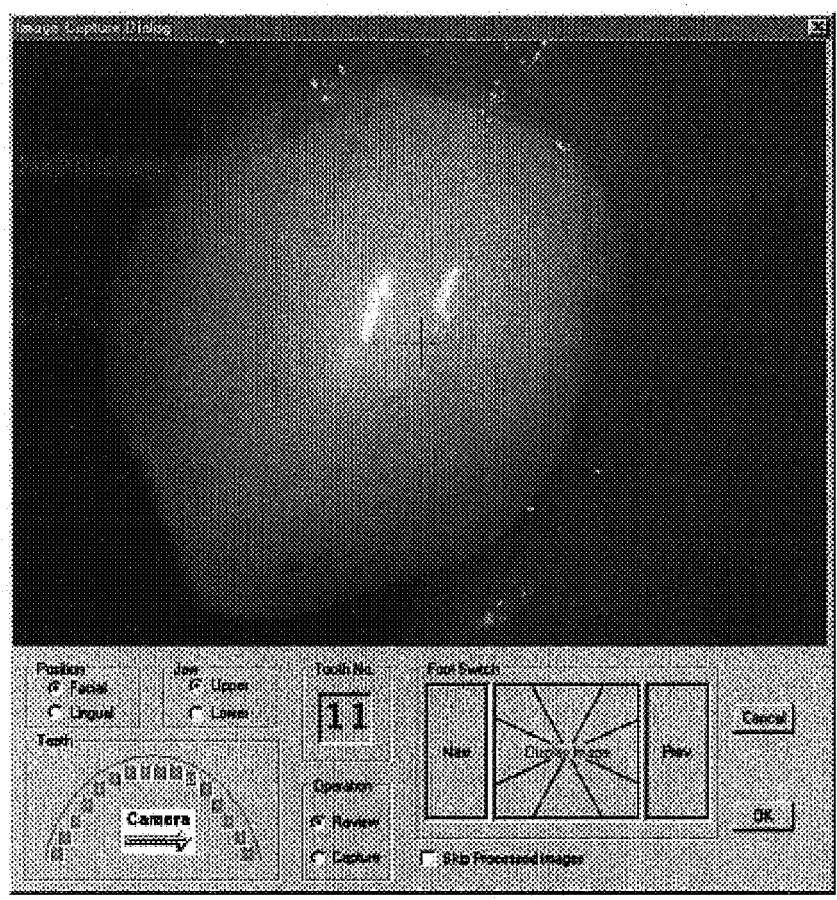
Figure 2C:
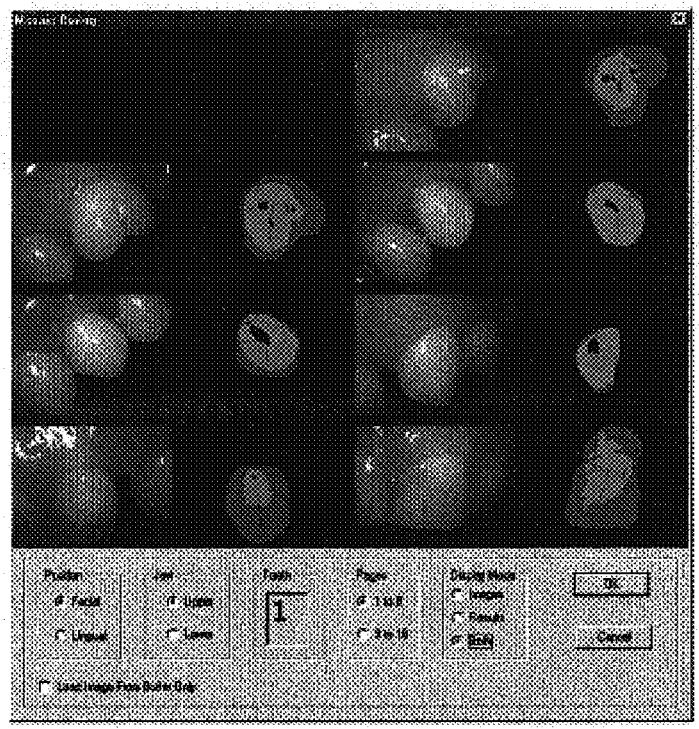

Among the features of the software that allows easy use of the system and method are utilities to create brushes, patients, clinicians, etc. on the fly and assign them to any arbitrary study dynamically (as shown in FIG. 2A), capture images swiftly in any sequence (as shown in FIG. 2B), and review the results on all teeth images simultaneously in a mosaic dialog (as shown in FIG. 2C) upon completion of processing.

The automated and accurate processing of the captured images to detect plaque on a tooth-by-tooth basis enable performance of clinical trials and analysis with minimal human intervention. These features offer distinct advantages over the related art systems. The system and method include an image segmentation technique that robustly segments an object from surrounding background (e.g., gums) and adjacent overlapping objects (e.g., teeth). A graphics morphing procedure automatically divides any arbitrary tooth into several regions (grids) using a procedure that is robust to teeth orientation changes. This is a nontrivial task due to the large variations in teeth shapes, sizes, and orientation within the mouth. Each of the main components of the system and method of the presented invention is discussed in turn.

A. Object Segmentation

Object segmentation involves the automated determination of object regions of interest in the presence of surrounding background clutter, noise, and other objects. Numerous object segmentation methods have been designed for various applications.

The segmentation technique used for a specific application depends on the constraints of the problem being solved, including image, color, shape, and texture variability. Stochastic and statistical methods are commonly used for image segmentation of natural scenes where the object structure is not fixed or deterministic. Non-causal Markov models and causal Markov models have been used for supervised and unsupervised segmentation of textured images of natural scenes. These stochastic methods involve initial pixel labeling using the Markov model parameters or texture features and gray-intensity information, followed by iterative maximum-a-posteriori ("MAP") re-labeling of the segmented data. In addition, autoregressive models, which in essence are Gaussian Markov random fields, have also been used for texture segmentation. Such technologies are powerful when images are characterized by textured objects and do not contain definite structure. However, such techniques involve iterative model parameter estimation and stochastic relaxation for region labeling which makes the segmentation process slow and computationally intensive.

Statistical color-histogram approaches to image segmentation include multilevel thresholding using a histogram with peak-finding followed by region merging, and region-adjacency graphs to merge adjacent regions while considering color statistical information. These techniques do not work well with teeth due to the close color similarities between plaque and gum regions in tooth images.

Geometrical edge-based contour models have been used for object detection and segmentation. One of the most recent popular approaches includes active contour models or snakes where an initial curve is defined and evolved based on true image gradient/edge information or level set functions that describe regional texture information. Geometrical models, called active shape models, and variations have been proposed where the object boundary is described as a series of line segments for all training images. The mean and the principal components of these line segments from training data are used to describe and constrain the variability in each line segment. For an unknown image, the line positions are moved within the constraints of the training sample principal components. Active contour and active shape model techniques are sensitive to the initial placement of the contour. The initial position needs to be close to the true position. However, this is not possible for teeth where the sizes, orientation and positions widely vary.

One of the most robust and quick object segmentation schemes involves a watershed algorithm. A philosophically similar edge-based segmentation method utilizes a predictive model to identify the direction of change in color and texture at each image pixel, thereby creating an edge flow vector. The edge flow vectors are propagated to locate the object boundaries. Initial comparison of the standard gray-watershed algorithm on edge images with the edge-flow technique yields similar segmentation results on teeth images. However, the edge-flow technique performs significantly slower (more than ten to one-hundred times slower) and therefore is not practical for a real-time application where segmentation speed is an important consideration.

The system and method of the present invention utilizes a novel, modified watershed segmentation algorithm that yields superior object segmentation compared to the standard watershed method. The standard gray and binary watershed algorithms are discussed below, followed by a discussion of the modified watershed algorithm of the present invention.

1. Gray Watershed Algorithm

Figures 3A, 3B, 3C, 3D:
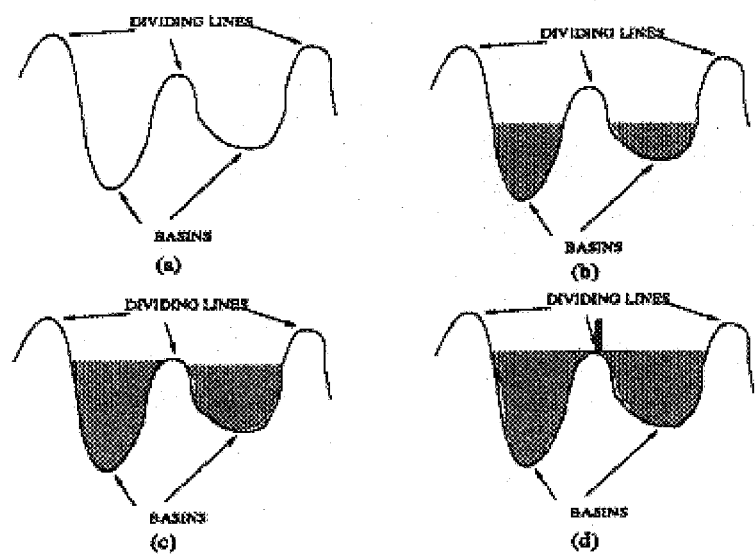
FIGS. 3A-3D are graphs providing an intuitive explanation of the conventional gray watershed algorithm.

This standard algorithm is useful for segmenting an object from surrounding clutter. It is applied to gray-scale input images. FIGS. 3A-3D depict the steps in the algorithm applied to a one-dimensional gray-scale profile. In the standard gray watershed algorithm, the center of each object is assumed to have the highest pixel gray-scale value, with lower values at the object edges. This gray-scale two-dimensional image/one-dimensional profile is then complemented so that object centers have the lowest values. FIG. 3A shows a hypothetical complemented one-dimensional scan line of a gray-scale image of a cluster of two touching objects. It has basins (minima) at the center of each object. The algorithm is best described by envisioning filling this contour with water, where FIGS. 3B-3D show different water levels in the basins. This results in the different basins being filled to equal heights. When the water overflows between two adjacent basins, the corresponding ridges or watersheds locate the dividing lines between basins, or in the current problem, the boundary between adjacent nuts (each nut corresponds to a separate basin).

2. Binary Watershed Algorithm

The binary watershed algorithm is another segmentation algorithm similar to the gray watershed algorithm, and has many variations. This algorithm works well when objects have a prominent boundary from surrounding boundaries and objects touch/overlap with each other to form clusters. It can be described in terms of erosions, but it is best implemented using the distance transform. In this case, the object cluster image is binarized and a distance transform of the binary object cluster is calculated. The gray watershed algorithm is applied to the gray-scale distance-transformed image. This combination is referred to as the binary watershed algorithm. To produce the distance-transformed image, an image is thresholded to obtain a binary blob. Each "on" pixel on an object is replaced by a gray-scale value equal to its distance from the nearest edge in the object cluster boundary. FIG. 4B shows an example of the distance transform image of FIG. 4A. Its cross-section (FIG. 4C) shows two well-defined peaks and is much better than the cross-section produced from the original gray-scale image. FIG. 4D shows the complement of the cross-sectional plot in FIG. 4C. Note the prominent valleys (centers of the nuts) and the peak (the dividing line between the nuts). The gray watershed transformation of FIG. 4D yields the final segmented image.

The gray watershed algorithm works well if the objects to be segmented have slowly varying continuous gray levels. The algorithm fails on objects having large internal gray-scale variations, resulting in oversegmentation (where an object is subdivided into several regions), or if the boundary between the object and surrounding background is not characterized by a sufficient gray-scale change. FIG. 5A shows an example of touching objects where the large gray-scale variation in each object is shown as a one-dimensional profile in FIGS. 5B and 5C. The gaps by the shells in these objects can cause significant problems since they occur as local minima. The standard gray-scale watershed algorithm labels prominent local minima as object boundaries thereby resulting in oversegmentation. FIG. 5D shows a typical tooth image where the central tooth is surrounded by other teeth and gum regions (background). The contrast between the tooth and gum regions is hardly noticeable. Additionally, the presence of glare regions caused by reflections due to the camera light causes high color intensity changes within the tooth. Therefore, the standard gray watershed algorithm does not work well on these teeth images. Smoothing the image with a Gaussian filter to reduce the effect of local peaks and valleys (to produce smooth images of each object) was considered, but this also further reduced contrast between tooth boundaries.

The standard binary watershed algorithm has over-segmentation problems when the object boundary is irregular or complex. Extra segmented regions and boundary lines were also formed when the objects were not oval or elliptical (this occurs for teeth). In addition, the binary watershed works well for segmenting two or more touching objects when the boundary between object and background is well-defined. In teeth, the boundary between teeth and gum is often ill-defined as shown in FIG. 5D. Thus, the standard binary watershed algorithm does not work well on segmenting teeth.

3. Modified Watershed Segmentation

The system and method of the present invention utilizes a two-stage watershed algorithm that robustly segments low-contrast objects while handling color/gray-scale variations within the object. Prior to segmentation, the data is preprocessed to handle variations in lighting conditions and variations in object color and contrast. Then a two-stage watershed-based segmentation is performed, followed by post-processing.

a. Data Processing

Images of objects often have variations in dynamic range and color from image to image due to differences in illumination intensity (caused by different light bulb sources), variations in distance between objects and a light source (intensity is inversely proportional to distance between the light and the object), differences in camera hardware (e.g., hue, saturation setting of the CCD camera, etc.), and variations in the contrast between the object and the background. Data processing is therefore needed for proper segmentation and classification.

Since there is significant variation in teeth color due to the above-mentioned reasons, a normalized edge contrast map is extracted to handle differences in illumination conditions and camera settings. The input color image is first filtered using edge kernels in each color channel. Gabor edge filter kernels may be used since their scale can be easily changed mathematically and they have the best joint space-frequency resolution among all filters. Imaginary Gabor edge filters have been used extensively in prior work for target recognition, image compression, and recognition of handwritten addresses on envelopes, among other applications. The Gabor filter outputs from each color channel are weighted and added, to yield a single gray-scale edge (contrast) image. This handles variations in average color between objects and background in different images caused by changes in illumination intensity and/or camera settings.

To handle contrast variability, each edge image is normalized based on the variance of the edge image. The variance of each edge image is computed and each pixel edge value is divided by the image variance. This yields an output edge image with unit variance. This image is then normalized to ensure that pixels with excessively high values do not skew the image data. This normalization ensures that images with different contrasts have similar normalization output values. FIG. 6A shows a high-contrast tooth where the enamel-gum boundary is clearly visible. FIG. 6B shows the Gabor edge-normalization output image. FIG. 6C shows a tooth image with low-contrast between enamel and gum and FIG. 6D shows the corresponding output image having good normalization contrast. The white spots in both edge images are glare regions that are masked prior to segmentation.

b. Object Segmentation Algorithm

The two-step watershed algorithm for segmenting objects of the present invention is robust to images with low object-boundary contrast and large internal color/gray-scale variations. This involves determination of the central portion of the object with one watershed using the center of the object as the seed point. This is followed by a reverse watershed using the external boundary surrounding the object and the internal portion of the object as two seed regions. The points at which these two regions meet correspond to the true object boundary.

The first stage of the segmentation algorithm involves locating a few pixels on the object of interest. This can be resolved by one of several techniques, depending upon prior knowledge of the specific application being addressed. The tooth enamel, which is a part of the tooth of interest, is typically close to the center of the image and is the brightest portion of the image due to the incident light and their natural color. Therefore, a cumulative histogram-based method is used to locate a few pixels in the object of interest. Since the dye used assigns a red color to plaque on teeth and gum regions, the red channel is not useful for discriminating between tooth and boundary regions. However, class-specific useful information is present in the green and blue channels. The cumulative histogram for each of the other color channels, green (CHG) and blue (CHB) is determined. The color values (TG and TB) that correspond to the brightest 12.5 percent (%) of the pixels in each color channel are then determined. Two binary images (BG and BB) are formed by thresholding each of the color channels at the thresholds (TG and TB) and these binary images are combined to yield a single binary image, where the brightest enamel regions in the image are labeled as one (1). This corresponds to finding the brightest 12.5% of the regions in both the blue and green channels combined. The algorithm then labels each connected "on" (white) region in the binary thresholded image with a unique color—this process is called "blob-coloring." The blob-colored (labeled) image is then analyzed and the area of each blob region is computed. The algorithm then extracts the largest blob greater than an area (AE) closest to the image center. This corresponds to the central portion of the tooth of interest in the image. This seed region (SR1) is labeled as one (1) and the rest of the image pixels are assigned to zero (0). FIGS. 7A-7C show an example of the technique to determine the starting seed region for segmentation.

The seed region is then used as a starting point on the watershed algorithm applied to the edge map of the color image, as described earlier in Section A.3.a. The watershed algorithm threshold (TW1) used in the first stage is very low to allow for detection of a tooth-gum boundary when the image contrast is small. This is the maximum allowable change in edge value (or maximum allowable edge peak value) in the Gabor edge-map to form a new region in the segmentation procedure during region growing. This low value for TW1 ensures that object undersegmentation does not occur at this stage. Undersegmentation occurs when a true boundary between an object and boundary is not detected, thereby resulting in fewer segmented regions in the image that are actually present. However, object oversegmentation could occur if a low threshold is used. This occurs when a single object is segmented into two or more regions. This could occur because of large color/gray-scale variations within the object (e.g., due to the presence of plaque around the center of the tooth, glare, enamel surface changes, or other illumination effects). FIGS. 8A-8C show an example of the watershed segmentation of the image in FIG. 7A using the seed region in FIG. 7C as the starting point. The edge map in FIG. 8A is used as the input image. Note the oversegmentation result in FIG. 8B. The color variation due to the plaque region close to the tooth center and the plaque close to the gum line produce spurious segmented regions cause this oversegmentation. The region that is connected to the set of original seed points is selected as the segmented object (tooth) of interest, as shown in FIG. 8C. This central segmented region is referred to as S1.

The first stage of segmentation typically yields an oversegmented object, as shown in FIGS. 8A-8C. To accurately locate the true object boundary, the system and method of the present invention implements a new reverse watershed algorithm where the background regions and the object region that meet during the process of growing each region are labeled as the true object boundaries. If the object region was grown alone, parts of the background could be labeled as the object if the true object-background had low contrast. If too much color variation occurs within the object, object oversegmentation will occur. Growing the background region alone is not a good alternative since parts of the object could be labeled as background if the true object-background boundary has low contrast. Additionally, parts of the background could be labeled as object (resulting in undersegmentation) if the background has too many color variations, due to the presence of other objects such as surrounding teeth around the central tooth. To avoid all these drawbacks, the object and background regions are grown simultaneously, which makes the segmentation process robust to low object-background contrast, while handling color variations within the object (tooth). The maximum allowable color variation (the watershed threshold) TW2 is specified high to avoid object oversegmentation. The surrounding background seed region can be chosen using prior knowledge about the application. A border region at a certain radius R outside the object region from stage 1, S1, is used as the background seed region.

FIGS. 9A-9C show the seed background region chosen with R=70 pixels away from the object seed border. The regions are grown simultaneously using the watershed algorithm. The final segmented regions are shown with different labels in FIG. 9B, and the object boundary superposed on the tooth image in FIG. 9C illustrates the accuracy of the segmentation algorithm. The plaque regions on the tooth around the gum border (bottom portion) and on the biting surface of the tooth (top portion) and the central part of the tooth that resulted in spurious regions in the first stage of segmentation (FIG. 8B) are labeled as part of the tooth in this stage.

B. Object Grid Morphing

Figures 10A, 10B, 10C, 10D:
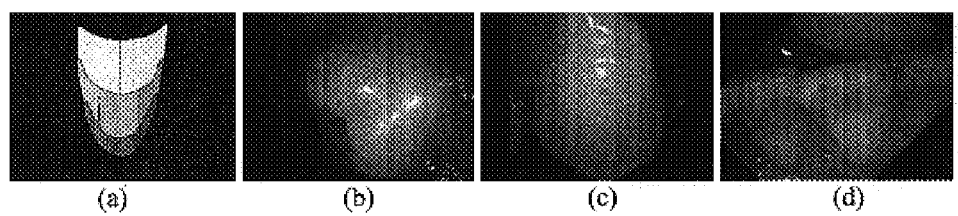
FIG. 10A shows a grid provided on template synthetic tooth.
FIGS. 10B-10D are images showing the various shapes and sizes of real teeth.
Figure 11A:
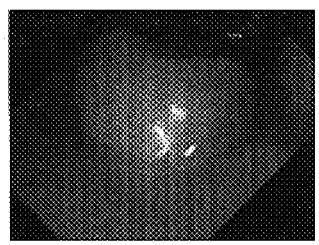
FIGS. 11A-11D are examples of two teeth images where the grids are automatically overlaid onto the segmented teeth using the template grid of FIG. 10A.
Figure 11B:
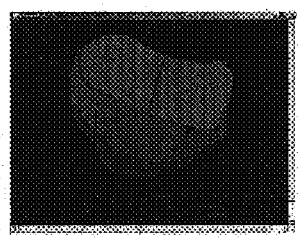
Figure 11C:
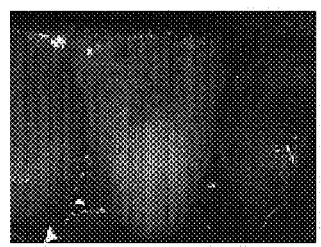
Figure 11D:
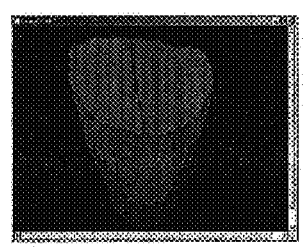

After locating the tooth of interest, the tooth has to be divided into a number (e.g., eight) of regions (excluding the biting surface). This division of the tooth into eight regions or grids yields accurate information about the presence or absence of plaque on different parts of the tooth. This detailed information can be used to predict the efficacy of plaque removal on different parts of each tooth using various toothbrushes. For example, certain toothbrushes could be efficient at removing plaque from the biting surface of a tooth, but not from the gingival margin. A grid on a template synthetic tooth is shown in FIG. 10A. There is no fixed rule for overlaying a grid onto a real-tooth. Assigning an area-based rule, or a position-based rule to overlay a grid on an arbitrary tooth is a difficult task due to the wide variation in shape, size, orientation, asymmetry, and irregularities between different teeth that is further complicated by the variation in distance between the camera and the tooth. Examples of the variety of tooth shapes, sizes, asymmetry, etc. are shown in FIGS. 10B-10D.

Due to this inconsistency in being able to develop a specific rule for overlaying a grid onto such a wide variety of shapes, the system and method of the present invention employ a computer-graphics based morphing procedure to draw a grid on any arbitrary tooth shape.

Several morphing procedures have been implemented in prior work. The most relevant techniques include mesh-based warping by distortions of regular grids and extensions to these using deformable snakes. These mesh-based methods have problems such as requiring the same number of polygons in each model, or when topologies of each object differ (such as the presence of a hole).

One of the most flexible and effective morphing procedures involves describing the objects of interest using lines.

These lines are the salient features that describe the object. For example, the lines that describe a human face would be those along the eyes, mouth, nose, chin, ears, hairline, etc. When it is desired to morph one object into another object, the line correspondences between each object is first determined. This is typically done by hand in prior work since finding the line correspondences between the two objects is critical to obtaining good morphing results. In order to warp from one source image to a destination image, the goal is to find the pixel correspondence between the source and destination images. A pixel in the source image is a function of the pixel location in the destination image and a weighted distance to each line describing the object.

The present invention employs this line-based morphing procedure to overlay a grid automatically on each segmented tooth. One challenge in the warping procedure is building the correspondence between lines in the source and destination images. These lines are typically hand-drawn and the line correspondences are manually selected. When the object size between the source and destination objects differs greatly, and when the shapes are not similar, the correspondence problem magnifies further. In the present invention, the source image is the template grid shown in FIG. 10A, and the destination image corresponds to a segmented tooth. The procedure defines an efficient method to describe a segmented tooth boundary through lines, and automatically builds line correspondences between the template and a tooth image.

Given a binary segmented object, the center of gravity $(C_x, C_y)$ of the binary blob is first determined. The topmost X coordinate of the blob that lies above the center of gravity is noted as $(C_{Tx}, C_y)$. The number of lines to represent the boundary is defined as $N_B$. The points of a boundary representing a segmented object are listed as a chain code (an order representation of the boundary points in clockwise fashion), where the boundary starts at $(C_{Tx}, C_y)$ and proceeds in a clockwise manner. This set of points is then subsampled using digital Fourier transforms to yield $N_{B-1}$ points that represent the boundary of that object. This subsampling results in $N_B$ lines regardless of the size of the object boundary, where the starting point is the topmost point in the segmented object above its center of gravity. The subsampling is also robust to "noise" in the segmented image boundary caused by artifacts of the segmentation process. This line representation using $N_B$ lines is used for both, the template tooth and any segmented object blob. This yields a line representation of the template and an arbitrary object with an automatic correspondence between each of them. The line-based warping rule is then applied to these images with the template grid (FIG. 10A) as the source image. The warping results in a grid being warped onto the destination segment image. FIGS. 11A-11D show examples of two teeth images where the grids are automatically overlaid onto the segmented teeth using the template grid in FIG. 10A. The morphing results are excellent even when the shapes of the tooth differ significantly from that of the template synthetic tooth image.

C. Plaque Classification

The last step in the system and method of the present invention involves classification of plaque regions on the tooth images. The segmented teeth primarily consist of three types of regions: enamel, glare, and plaque. The classification of glare regions is simple due to their unusually bright color values. Enamel tends to be similar to plaque in many cases, so classification between plaque and enamel is often more difficult. A three-class Fisher Linear Discriminant (FLD) which is a Gaussian-based linear pattern recognition classifier is used for this classification. The mean and covariance matrices of each class are estimated using the red, green, and blue (RGB) values for training image regions as input.

D. EXAMPLES

The system and method of the present invention will be further clarified by the following examples, which are intended to be purely exemplary of the invention. The results of all the significant components of the system and method are discussed herein. For all algorithms, a training set of sixty-four images from a randomly selected patient record (e.g., patient A) was used. The training set was used to determine the segmentation algorithm parameters and the plaque classification matrices for the three classes. An independent test set of sixty-four images of another randomly selected patient (e.g., patient B) was used as the test set to test the performance of the algorithms.

1. Object Segmentation

The segmentation method of the present invention performed significantly better than the normal watershed segmentation on the edge image. In order compare the performance of the modified watershed segmentation of the present invention versus the original watershed algorithm, a subset of ten typical teeth images was selected from the test patient examination record, out of the sixty-four test set images. The teeth segmentation parameters were selected based on the performance of the segmentation algorithm on a set of sixty-four training set images of patient A.

The two types of errors that can occur during segmentation are undersegmentation and oversegmentation. Oversegmentation occurs when the object of interest is divided into several regions after completion of segmentation. This implies that only a part of the object is correctly detected if oversegmentation occurs. An E % oversegmentation error occurs when E % of the tooth is not detected after segmentation. Undersegmentation occurs when the segmentation method labels parts of the background as belonging to the object. Therefore, the resultant region will contain other objects besides the object of interest. An E % undersegmentation error occurs when E % of the segmented region contains pixels that do not actually belong to the tooth of interest.

The segmentation results of the segmentation algorithm of the present invention and the standard watershed algorithm are shown in Table 1 below. The dual watershed segmentation algorithm of the present invention outperforms the standard watershed on the average segmentation error per image (4.6% average error versus 16.7% average error). A certain amount of segmentation error of about 10% is expected and tolerable for this application. As many as six tooth images (out of 10) have greater than 15% segmentation error when the standard watershed algorithm is used, whereas the dual watershed does not have any images with a more than 15% segmentation error.

TABLE 1

|  | Average total segmentation error (%) | No. of teeth (out of 10) with >5% segmentation error | No. of teeth (out of 10) with >15% segmentation error |
| --- | --- | --- | --- |
| Dual watershed | 4.6% | 2 | 0 |

TABLE 1-continued

| | Average total segmentation error (%) | No. of teeth (out of 10) with >5% segmentation error | No. of teeth (out of 10) with >15% segmentation error |
|---|---|---|---|
| Standard watershed | 16.7% | 9 | 6 |

FIGS. 12A and 12B show segmentation result images of the dual watershed segmentation of the present invention versus the standard watershed. The dual watershed segmentation boundaries are shown as lines superposed on the original color teeth image in FIG. 12A. The standard watershed regions after segmentation are shown as different gray-valued regions in FIG. 12B. The standard watershed typically oversegments the tooth of interest due to color variations within a tooth, as seen in the left and center images in FIGS. 12A and 12B. The standard watershed is unable to detect part of the enamel in the image at the right in FIGS. 12A and 12B. The dual watershed algorithm of the present invention undersegments the tooth due to the low contrast of the image, but is able to detect the tooth enamel.

The segmentation results on all the sixty-four test images using the dual watershed algorithm of the present invention are shown in Table 2 below. The average segmentation error was 8.1%, including 6.3% oversegmentation errors and 14.4% undersegmentation errors. Note that the average segmentation error is below the tolerable (allowable) segmentation error of around 10%. As seen in Table 2, only 14% of the teeth in the test set had a segmentation error of more than 10%. This is quite good, given the variability in color, contrast, and other variations in the teeth images. As expected, most of the undersegmentation errors were caused by low-contrast images where the boundary between the tooth and background is not clearly visible. FIG. 13A shows an example where the tooth is undersegmented because the boundary between the central tooth and the surrounding teeth is of very low-contrast compared with the glare regions, and the boundary between the enamel and gum regions. An example where tooth segmentation occurs due to the presence of tooth filling at the center of the tooth is shown in FIG. 13B.

TABLE 2

| | Avg. Seg. Error (%) | % Teeth (out of 64( with >5% Seg. Error | % Teeth (out of 64( with >10% Seg. Error | % Teeth (out of 64( with >20% Seg. Error | Avg. OverSeg. Error (%) | Avg. UnderSeg. Error (%) |
|---|---|---|---|---|---|---|
| Dual Watershed | 8.1% | 21.7% | 14% | 12.5% | 6.3% | 14.4% |

2. Grid Morphine Results

Figure 14A:
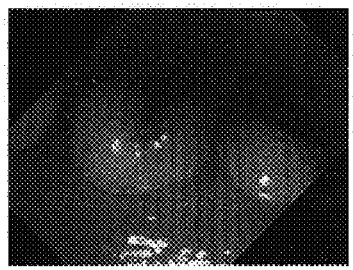
FIGS. 14A-14D are images showing the grid morphing results (FIGS. 14B and 14D) for tooth images (FIGS. 14A and 14C), respectively.
Figure 14B:
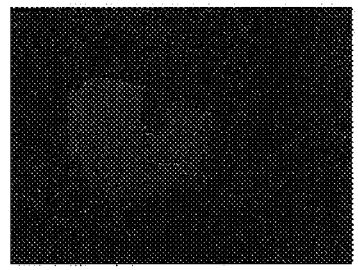
Figure 14C:
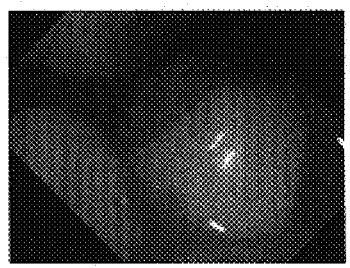
Figure 14D:
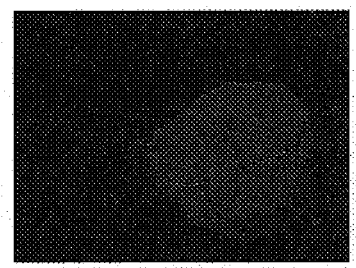
Figure 15A:
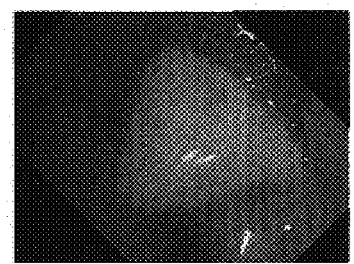
FIGS. 15A-15D are examples of a classified labeled output image. green indicates enamel, and black indicates glare.
Figure 15B:
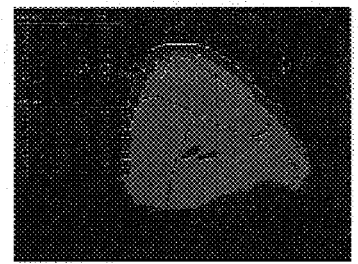
Figure 15C:
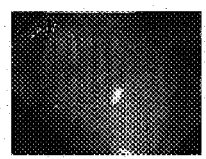
Figure 15D:

Due to the wide differences in size, shape, and orientations of teeth, the problem of overlaying a grid onto each tooth automatically is a non-trivial task. Since there is no standard rule by which a grid can be drawn onto an arbitrary tooth, the performance of the automated grid morphing procedure is incapable of being numerically described. Therefore, an analysis was based on visual examination of the grid-morphing results. The automatic grid morphing worked robustly and gave intuitively appealing results for all cases where the tooth had odd shapes. FIG. 14A shows a case where the biting surface of the tooth is missing, thereby creating an awkward-shaped boundary. However, the resultant grid morphed onto this shape, using the template of FIG. 10A, fits this shape very well. The automated grid morphing procedure of the present invention also works robustly when the tooth is oriented away from the vertical line, as seen for the tooth in FIG. 14C which is slanted to the left.

3. Plaque Classification Results

A three-class Fisher Linear Discriminant (FLD) linear pattern recognition classifier was used. The mean and covariance matrices of each class (plaque, enamel, and glare) were estimated using the red, green, and blue (RGB) values from the sixty-four training image-set. These sample three-by-one mean and three-by-three covariance matrices were then used to classify the test-set images. The plaque classification results were excellent. The three-class confusion matrix is shown in Table 3 below. Only 3.1% of the plaque regions were incorrectly classified as plaque. This error typically occurs when the captured images are blurred due to camera motion. This reduces the contrast and color of plaque regions. Glare regions are easily distinguishable from enamel and plaque. FIGS. 15A-15D show examples of the classified labeled output image. Note that plaque is detected well (FIGS. 15C and 15D) even when the plaque is present on the enamel surface that is not well lit. If desired, a red color may indicate plaque, a green color may inficate enamel, and a black color may indicate glare.

TABLE 3

| True class (rows)/ classified as (columns) | Plaque | Enamel | Glare |
|---|---|---|---|
| Plaque | 96.9% | 3.1% | 0% |
| Enamel | 1.8% | 98.2% | 0% |
| Glare | 0% | 0% | 100% |

The system and method of the present invention provide many advantages over the related art. For example, the system and method enable automated evaluation of toothbrush designs for removing plaque in clinical trial settings. A major component of the system and method is the development of a new segmentation technique that robustly segments objects in the presence of variable lighting, contrast, color, and noisy backgrounds. This segmentation procedure was shown to work effectively on images captured during the course of clinical trials. It was shown to significantly outperform the conventional watershed segmentation procedure. The system and method of the present invention also provides a technique to automatically determine the line correspondences in the Beier-Neely morphing procedure. This is a significant component to achieve automated morphing from one arbitrary shape to another.

The system and method of the present invention also includes utilities to dynamically group patients together into examination studies, with different brushes used either in parallel or across different groups of patients (in different studies) and software to generate plaque removal efficacy information for different brushes on combinations of teeth, and for combinations of teeth grid regions. This capability to do automated plaque analysis on an individual tooth-by-tooth basis with grid information data is new and is not believed to have been achieved in the dental community so far.

It will be apparent to those skilled in the art that various modifications and variations can be made in the computer-implemented system and method for automatically evaluating the efficacy of plaque removal and whitening capabilities for different toothbrushes and toothpastes of the present invention and in construction of this system and method without departing from the scope or spirit of the invention. As an example, the system and method may include automatic procedures to determine the image preprocessing parameters (such as the edge-image normalization parameters), depending upon each individual image, methods to handle segmentation when other dyes are used for plaque detection, and methods to handle more angular variations of teeth orientation in the morphing procedure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for automatically evaluating the efficacy of plaque removal and whitening capabilities for different toothbrushes and toothpastes on a tooth-by-tooth basis in real-time, comprising:
    determining a central portion of each tooth with a watershed segmentation algorithm using a center of each tooth as a seed point;
    applying a reverse watershed segmentation algorithm using an external boundary surrounding each tooth and an internal portion of each tooth as two seed regions, wherein the point at which the two seed regions intersect correspond to the actual tooth boundary;
    applying a line-based morphing procedure to automatically overlay a grid on each segmented tooth; and
    classifying plaque regions of each tooth.

2. A method as recited in claim 1, wherein prior to the central portion determination, the method further comprises:
    preprocessing data about each tooth to handle variations in lighting conditions and in the color and contrast of each tooth.

3. A method as recited in claim 2, wherein the preprocessing data comprises:
    filtering an input color image of the data using edge kernels in each color channel to output edge images; and
    normalizing each edge image based upon a variance of each edge image.

4. A method as recited in claim 1, wherein the central portion determination comprises:
    locating a few pixels on each tooth by determining a cumulative histogram for color channels;
    finding the brightest regions in the color channels; and
    extracting the largest color region closest to the central region of each tooth.

5. A method as recited in claim 1, wherein the applying a reverse watershed segmentation algorithm comprises:
    growing each tooth region and a background region simultaneously; and
    labeling as true tooth boundaries the intersections of the tooth and background regions.

6. A method as recited in claim 1, wherein the applying a line-based morphing procedure comprises:
    determining a center of gravity of each segmented tooth;
    yielding a line representation of a template tooth and each tooth with an automatic correspondence between each; and
    applying a line-based warping rule to produce a grid warped onto each segmented tooth.

7. A method as recited in claim 1, wherein classifying plaque regions of each tooth comprises using a three-class Fisher Linear Discriminant linear pattern recognition classifier.

8. A computer-implemented method for automatically evaluating the efficacy of plaque removal and whitening capabilities for different toothbrushes and toothpastes on a tooth-by-tooth basis in real-time, comprising:
    determining a central portion of each tooth with a watershed segmentation algorithm using a center of each tooth as a seed point;
    applying a reverse watershed segmentation algorithm using an external boundary surrounding each tooth and an internal portion of each tooth as two seed regions, wherein the point at which the two seed regions intersect correspond to the actual tooth boundary;
    applying a line-based morphing procedure to automatically overlay a grid on each segmented tooth; and
    classifying plaque regions of each tooth.

9. A computer-implemented method as recited in claim 8, wherein prior to the central portion determination, the method further comprises:
    preprocessing data about each tooth to handle variations in lighting conditions and in the color and contrast of each tooth.

10. A computer-implemented method as recited in claim 9, wherein the preprocessing data comprises:
    filtering an input color image of the data using edge kernels in each color channel to output edge images; and
    normalizing each edge image based upon a variance of each edge image.

11. A computer-implemented method as recited in claim 8, wherein the central portion determination comprises:
    locating a few pixels on each tooth by determining a cumulative histogram for color channels;
    finding the brightest regions in the color channels; and
    extracting the largest color region closest to the central region of each tooth.

12. A computer-implemented method as recited in claim 8, wherein the applying a reverse watershed segmentation algorithm comprises:
    growing each tooth region and a background region simultaneously; and
    labeling as true tooth boundaries the intersections of the tooth and background regions.

13. A computer-implemented method as recited in claim 8, wherein the applying a line-based morphing procedure comprises:
    determining a center of gravity of each segmented tooth;
    yielding a line representation of a template tooth and each tooth with an automatic correspondence between each; and
    applying a line-based warping rule to produce a grid warped onto each segmented tooth.

14. A computer-implemented method as recited in claim 8, wherein classifying plaque regions of each tooth comprises using a three-class Fisher Linear Discriminant linear pattern recognition classifier.

15. A system for automatically evaluating the efficacy of plaque removal and whitening capabilities for different toothbrushes and toothpastes on a tooth-by-tooth basis in real-time, comprising:
   a memory configured to store instructions; and
   a processor configured to execute the instructions stored in the memory, the instructions being for:
      determining a central portion of each tooth with a watershed segmentation algorithm using a center of each tooth as a seed point,
      applying a reverse watershed segmentation algorithm using an external boundary surrounding each tooth and an internal portion of each tooth as two seed regions, wherein the point at which the two seed regions intersect correspond to the actual tooth boundary,
      applying a line-based morphing procedure to automatically overlay a grid on each segmented tooth, and
      classifying plaque regions of each tooth.

16. A system as recited in claim 15, wherein prior to the central portion determination instructions, the processor executes further instructions for:
   preprocessing data about each tooth to handle variations in lighting conditions and in the color and contrast of each tooth.

17. A system as recited in claim 16, wherein the preprocessing data instructions comprise:
   filtering an input color image of the data using edge kernels in each color channel to output edge images; and
   normalizing each edge image based upon a variance of each edge image.

18. A system as recited in claim 15, wherein the central portion determination instructions comprise:
   locating a few pixels on each tooth by determining a cumulative histogram for color channels;
   finding the brightest regions in the color channels; and
   extracting the largest color region closest to the central region of each tooth.

19. A system as recited in claim 15, wherein the applying a reverse watershed segmentation algorithm instructions comprise:
   growing each tooth region and a background region simultaneously; and
   labeling as true tooth boundaries the intersections of the tooth and background regions.

20. A system as recited in claim 15, wherein the applying a line-based morphing procedure instructions comprise:
   determining a center of gravity of each segmented tooth;
   yielding a line representation of a template tooth and each tooth with an automatic correspondence between each; and
   applying a line-based warping rule to produce a grid warped onto each segmented tooth.

21. A system as recited in claim 15, wherein classifying plaque regions of each tooth instructions comprise using a three-class Fisher Linear Discriminant linear pattern recognition classifier.

22. A computer readable medium stores instructions executable by at least one processor to perform a method for automatically evaluating the efficacy of plaque removal and whitening capabilities for different toothbrushes and toothpastes on a tooth-by-tooth basis in real-time, comprising:
   instructions for determining a central portion of each tooth with a watershed segmentation algorithm using a center of each tooth as a seed point;
   instructions for applying a reverse watershed segmentation algorithm using an external boundary surrounding each tooth and an internal portion of each tooth as two seed regions, wherein the point at which the two seed regions intersect correspond to the actual tooth boundary;
   instructions for applying a line-based morphing procedure to automatically overlay a grid on each segmented tooth; and
   instructions for classifying plaque regions of each tooth.

23. A computer readable medium as recited in claim 22, wherein prior to the central portion determination instructions, the computer readable medium further comprises:
   instructions for preprocessing data about each tooth to handle variations in lighting conditions and in the color and contrast of each tooth.

24. A computer readable medium as recited in claim 23, wherein the preprocessing data instructions comprise:
   instructions for filtering an input color image of the data using edge kernels in each color channel to output edge images; and
   instructions for normalizing each edge image based upon a variance of each edge image.

25. A computer readable medium as recited in claim 22, wherein the central portion determination instructions comprise:
   instructions for locating a few pixels on each tooth by determining a cumulative histogram for color channels;
   instructions for finding the brightest regions in the color channels; and
   instructions for extracting the largest color region closest to the central region of each tooth.

26. A computer readable medium as recited in claim 22, wherein the applying a reverse watershed segmentation algorithm instructions comprise:
   instructions for growing each tooth region and a background region simultaneously; and
   instructions for labeling as true tooth boundaries the intersections of the tooth and background regions.

27. A computer readable medium as recited in claim 22, wherein the applying a line-based morphing procedure instructions comprise:
   instructions for determining a center of gravity of each segmented tooth;
   instructions for yielding a line representation of a template tooth and each tooth with an automatic correspondence between each; and
   instructions for applying a line-based warping rule to produce a grid warped onto each segmented tooth.

28. A computer readable medium as recited in claim 22, wherein classifying plaque regions of each tooth instructions comprise instructions for using a three-class Fisher Linear Discriminant linear pattern recognition classifier.

* * * * *